United States Patent

Kramer et al.

[11] 3,940,413
[45] Feb. 24, 1976

[54] 1-ETHYL-IMIDAZOLES

[75] Inventors: Wolfgang Kramer; Karl Heinz Buchel; Werner Meiser; Manfred Plempel, all of Wuppertal, Germany

[73] Assignee: Bayer Aktiengesellschaft, Germany

[22] Filed: Aug. 20, 1973

[21] Appl. No.: 390,042

[30] Foreign Application Priority Data

Aug. 29, 1972 Germany............................ 2242454

[52] U.S. Cl................................. 260/309; 424/273
[51] Int. Cl.$^2$....................................... C07D 233/60
[58] Field of Search.................................. 260/309

[56] References Cited

UNITED STATES PATENTS

| | | | |
|---|---|---|---|
| 3,575,999 | 4/1971 | Godefroi et al..................... | 260/309 |
| 3,755,349 | 8/1973 | Timmler, et al.................... | 260/309 |

OTHER PUBLICATIONS

Fieser et al., Advanced Organic Chemistry (Reinhold Pub. Corp., N.Y., 1961) pp. 432–444.

*Primary Examiner*—Henry R. Jiles
*Assistant Examiner*—C. M. S. Jaisle

[57] ABSTRACT

1-Ethyl-imidazoles of the formula

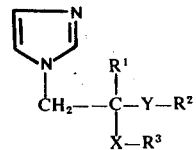

or a pharmaceutically acceptable nontoxic salt thereof, are produced by
a) reacting a compound of the formula

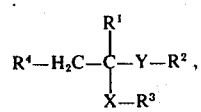

with imidazole; or
b) when $R^1$ is hydrogen, reacting a compound of the formula

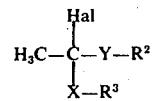

with imidazole in the presence of an acid binding agent. In the case of the salts the free base produced is reacted with an appropriate acid.
The 1-ethyl-imidazoles are useful for their antimycotic activity.

29 Claims, No Drawings

1-ETHYL-IMIDAZOLES

1-Ethyl-imidazoles of the formula

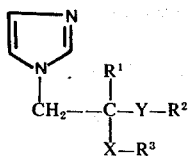

wherein
$R^1$ and $R^3$ are the same or different and are hydrogen, straight or branched-chain lower alkyl, straight or branched-chain lower alkenyl, cycloalkyl of 3 to 7 carbon atoms, cycloalkenyl of 5 to 7 carbon atoms, aryl of 6 to 10 carbon atoms unsubstituted or substituted by 1 to 3 of the same or different substituents selected from the group consisting of halogen, halogenoalkyl of 1 or 2 carbon atoms in the alkyl moiety and 2 to 5 halogen atoms, straight or branched-chain alkyl or 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethyl-substituted phenyl, or aralkyl of 6 to 10 carbon atoms in the aryl moiety and 1 to 4 carbon atoms in the alkyl moiety unsubstituted or substituted by 1 to 3 of the same of different substituents selected from the group consisting of halogen, halogenoalkyl of 1 or 2 carbon atoms in the alkyl moiety and 2 to 5 halogeno moieties, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl or hydroxymethyl-substituted phenyl;

$R^2$ is straight or branched-chain lower alkyl, straight or branched-chain lower alkynyl, cycloalkyl of 3 to 7 carbon atoms, cycloalkenyl of 5 to 7 carbon atoms, aryl of 6 to 10 carbon atoms unsubstituted or substituted by 1 to 3 of the same or different substituents selected from the group consisting of halogen, halogenoalkyl of 1 or 2 carbon atoms in the alkyl moiety and 2 to 5 halogeno moieties, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethyl-substituted phenyl, or aralkyl of 6 to 10 carbon atoms in the aryl moiety and 1 to 4 carbon atoms in the alkyl moiety unsubstituted or substituted by 1 to 3 of the same or different substituents selected from the group consisting of halogen, halogenoalkyl of 1 or 2 carbon atoms in the alkyl moiety and 2 or 5 halogeno moieties, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethylsubstituted phenyl;

X is a keto moiety or the moiety $-C(OR)_2$ wherein R is hydrogen or alkyl of 1 to 4 carbon atoms; and
Y is oxygen or sulphur; or a pharmaceutically acceptable nontoxic salt thereof, are produced by a. reacting a compound of the formula

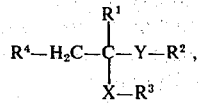

wherein $R^1$, $R^2$, $R^3$, X and Y are as above defined and $R^4$ is chlorine, bromine or hydroxy, with imidazole; or
b. when $R^1$ is hydrogen, reacting a compound of the formula

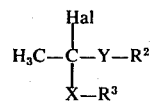

wherein $R^2$, $R^3$, X and Y are as above defined and Hal is halogen, with imidazole in the presence of an acid binding agent. In the case of the salts the free base produced is reacted with an appropriate acid.

The 1-ethyl-imidazoles are useful for their antimycotic activity.

More particularly the present invention is concerned with 1-ethyl-imidazoles of the formula

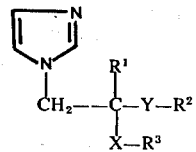

I and pharmaceutically acceptable nontoxic salts thereof wherein
$R^1$ and $R^3$ are the same or different, and are hydrogen, alkyl especially straight or branched-chain alkyl of 1 to 6 carbon atoms and especially 1 to 4 carbon atoms, alkenyl especially straight or branched-chain alkenyl of 2 to 6 carbon atoms and especially 2 to 4 carbon atoms, cycloalkyl of 3 to 7 carbon atoms and especially of 3, 5 or 6 carbon atoms, cycloalkenyl of 5 to 7 carbon atoms especially 5 or 6 carbon atoms, aryl especially of 6 to 10 carbon atoms and particularly phenyl unsubstituted or substituted by 1 or more preferably 1 to 3 and especially 1 or 2 of the same or different substituents selected from the group consisting of halogen especially fluorine, chlorine or bromine, halogenoalkyl of 1 or 2 carbon atoms in the alkyl moiety and 2 to 5 halogeno moieties especially chlorine or fluorine and particularly the trifluoromethyl moiety, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethyl-substituted phenyl, or aralkyl particularly of 6 to 10 carbon atoms in the aryl moiety and 1 to 4 carbon atoms in the alkyl moiety especially benzyl, unsubstituted or substituted by 1 or more preferably 1 to 3 and especially 1 or 2 substituents selected from the group consisting of halogen especially fluorine, chlorine or bromine, halogenoalkyl of 1 or 2 carbon atoms in the alkyl moiety and 2 to 5 halogeno moieties especially chlorine or fluorine and particularly the trifluoromethyl moiety, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl or hydroxymethyl-substituted phenyl;

$R^2$ is alkyl especially straight or branched-chain alkyl of 1 to 6 carbon atoms and especially of 1 to 4 carbon atoms, alkenyl particularly straight or branched-chain alkenyl of 2 to 6 carbon atoms and especially of 2 to 4 carbon atoms, cycloalkyl of 3 to 7 carbon atoms especially 3, 5 or 6 carbon atoms, cycloalkenyl of 5 to 7 carbon atoms especially 5 to 6 carbon atoms, aryl particularly of 6 to 10 carbon atoms and especially phenyl, unsubstituted or substituted by 1 or more preferably 1 to 3 and especially 1 or 2 of the same or different substituents selected from the group consisting of halogen especially fluorine, chlorine or bromine, halogenoalkyl of 1 or 2 carbon atoms in the alkyl moiety and 2 to 5 halogeno moieties especially chlorine or fluorine and particularly the trifluoromethyl moiety, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethyl-substituted phenyl, or aralkyl particularly of 6 to 10 carbon atoms in the aryl moiety and 1 to 4 carbon atoms in the alkyl moiety especially benzyl, unsubstituted or substituted by 1 or more preferably 1 to 3 and especially 1 or 2 substituents selected from the group consisting of halogen especially fluorine, chlorine or bromine, halogenoalkyl of 1 or 2 carbon atoms in the alkyl moiety and 2 to 5 halogeno moieties especially chlorine or fluorine and particularly the trifluoromethyl moiety, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl or hydroxymethyl-substituted phenyl;

X is a keto moiety of a functional derivative of a keto moiety, particularly a keto moiety or, when a functional derivative, the moiety —$C(OR)_2$ wherein R is hydrogen or alkyl preferably of 1 to 4 carbon atoms or X is an oxime or hydrazone; and Y is an oxygen or sulphur atom. These compounds are particularly useful because of their antimycotic activity.

The compounds of the present invention may be produced by:

a. reacting a compound of the formula

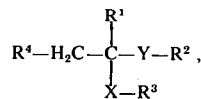

wherein $R^1$, $R^2$, $R^3$, X and Y are as above defined and $R^4$ is chlorine, bromine or hydroxy, with imidazole; or b. when $R^1$ is hydrogen, reacting a compound of the formula

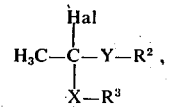

wherein $R^2$, $R^3$, X and Y are as above defined and Hal is halogen, with imidazole in the presence of an acid-binding agent.

The two processes of the present invention designated (a) and (b) above will be referred hereafter as Process Variants (a) and (b) respectively.

If 2-(2,5-dichlorophenoxy)-1-hydroxy-4,4-dimethyl-pentan-3-one and imidazole are used as starting compounds, the course of the reaction can be represented by the following equation (1) [Process Variant (a)]:

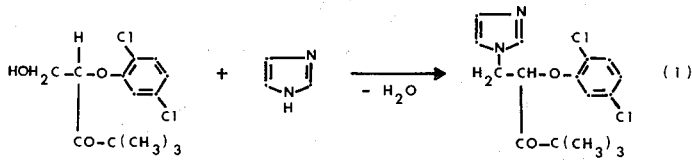

If 2-(2,5-dichlorophenoxy)-1-chloro-4,4-dimethyl-pentan-3-one and imidazole are used as starting compounds, the course of the reaction can be represented by the following equation (2) [Process Variant (a)]:

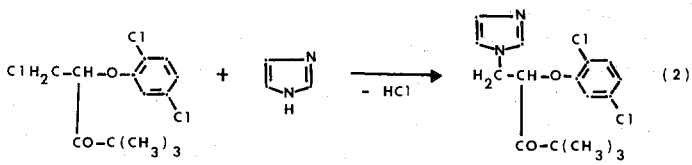

If 2-(2,5-dichlorophenoxy)-2-bromo-4,4-dimethyl-pentan-3-one and imidazole are used as starting compounds, the course of the reaction can be represented by the following equation (3) [Process Variant (b)]:

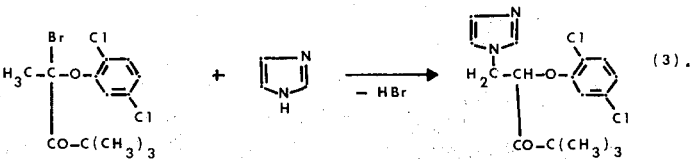

Process Variant (b) is a particularly chemically unobvious process since, surprisingly, and unforeseeably, the imidazole radical does not react with the α-carbon atom, which has acquired a free valency through the removal of the bromine atom, but instead reacts with the adjacent carbon atom of the methyl group.

When $R^1$ and $R^2$ and/or $R^3$ are alkyl moieties, the preferred moieties are methyl, ethyl, n-propyl, i-propyl, n-butyl, i-butyl, t-butyl, pentyl or hexyl, t-butyl being one preferred moiety, and when they are alkenyl moieties, the preferred moieties are vinyl, allyl, propenyl and hexenyl.

When $R^2$ is an alkinyl moiety, the preferred moieties are ethinyl, propinyl, butinyl or hexinyl.

When $R^1$, $R^2$ and/or $R^3$ is cycloalkyl or cycloalkenyl moiety, the preferred moieties are cyclopropyl, cyclopentyl, cyclohexyl, cycloheptyl, cyclopentenyl, cyclohexenyl or cycloheptenyl.

When $R^1$, $R^2$ and/or $R^3$ are aryl moieties or aralkyl moieties the preferred moieties are phenyl or benzyl, unsubstituted or substituted as hereinabove described.

When the aryl and aralkyl moieties, particularly phenyl or benzyl, are substituted, the preferred substituents are fluorine, chlorine, bromine, trifluoromethyl, methyl, ethyl, n-propyl, i-propyl, methoxy, ethoxy, thiomethyl, thioethyl, methylsulpho and ethylsulpho.

Hal in formula III is preferably chlorine or bromine, especially bromine.

According to one embodiment of the present invention, $R^1$ is hydrogen, $R^2$ is phenyl unsubstituted or substituted by 1 to 3 members selected from the group consisting of fluorine, chlorine, bromine, alkyl of 1 to 4 carbon atoms, alkoxy of 1 to 4 carbon atoms, trifluoromethyl, nitro, cyano and thioalkyl of 1 to 4 carbon atoms, or by one member selected from the group consisting of phenyl and hydroxymethylphenyl, or $R^2$ is benzyl unsubstituted or substituted by chlorine, bromine, fluorine or methyl, $R^3$ is lower alkyl, phenyl, benzyl or cyclohexyl, X is CO and Y is an oxygen atom.

According to another embodiment of the present invention $R^1$ is hydrogen, $R^2$ is phenyl unsubstituted or substituted by 1 to 3 members selected from the group consisting of chlorine, bromine and fluorine, by one member selected from the group consisting of chlorine, bromine and fluorine and an alkyl moiety of 1 to 4 carbon atoms or by 1 or 2 members selected from the group consisting of alkyl of 1 to 4 carbon atoms, alkoxy of 1 to 4 carbon atoms, trifluoromethyl, thioalkyl of 1 to 4 carbon atoms, nitro and cyano, or by phenyl or hydroxymethyl-substituted phenyl, or $R^2$ is benzyl unsubstituted or substituted by chlorine or methyl, $R^3$ is alkyl of 1 to 5 carbon atoms, phenyl, benzyl or cyclohexyl, X is CO and Y is an oxygen atom.

According to another embodiment of the present invention, $R^1$ is hydrogen, $R^2$ is phenyl unsubstituted or substituted by 1 to 3 chlorine, bromine or fluorine, by 1 chlorine, bromine or fluorine and 1 methyl group, by 1 or 2 methyl or methoxy groups, or by 1 methoxy, trifluoromethyl, nitro, cyano, thiomethyl, phenyl or hydroxymethyl-substituted phenyl group, or $R^2$ is benzyl unsubstituted or substituted by chlorine, or methyl, $R^3$ is methyl, t-butyl, pentyl, phenyl or benzyl, X is CO and Y is an oxygen atom.

The pharmaceutically acceptable, nontoxic salts of the compounds of the present invention are preferably the hydrogen halides, especially the hydrochloride and hydrobromide, the phosphate, the nitrate, mono-functional and bifunctional carboxylates and hydroxycarboxylates such as acetate, maleate, succinate, fumarate, tartrate citrate, salicylate, sorbate and lactate and the 1,5-naphthalene disulfonate. The salts are produced by reacting the free base with the corresponding acid, namely, the hydrogen halide acids such as the hydrochloric acid and hydrobromic acid, phosphoric acid, nitric acid, mono-functional and bifunctional carboxylic acids and hydroxycarboxylic acids such as acetic acid, maleic acid, succinic acid, fumaric acid, tartaric acid, citric acid, salicylic acid, sorbic acid and lactic acid and 1,5-naphthalene disulfonic acid.

The compounds of the formula II used as starting compounds in Process Variant (a), in which $R^4$ is hydroxy, are not previously known but can be produced by generally conventional methods. They are obtained, for example, when alcohols or thiols of the formula:

$$R^2YH \qquad IV,$$

wherein $R^2$ and Y are as above defined, are condensed in a known manner with halogenoketones of the general formula:

wherein $R^1$, $R^3$ and Hal are as above defined, and the resulting ether-ketones of the formula:

wherein $R^1$, $R^2$, $R^3$ and Y are as above defined, are reacted in a conventional way. The reaction may be carried out in the presence of alkali (for example aqueous sodium hydroxide solution) with formaldehyde or formaldehyde donors (for example a 40% strength aqueous formaldehyde solution) in an inert organic solvent (for example ethanol) at an elevated temperature, for example the boiling point of the reaction mixture. The desired products of general formula II are isolated and purified in the customary manner. The keto group can, if desired, be converted into a functional derivative in the customary manner.

The compounds of the formula II used as starting compounds in the Process Variant (a), in which $R^4$ is halogen, are not previously known but can be produced by conventional methods, for example by reacting an ether-ketone of the formula VI, as explained above, with formaldehyde or a formaldehyde donor in the presence of alkali and subsequently reacting the resulting compound of the formula II, in which $R^4$ represents OH, with a halogenating agent, such as thionyl chloride. The reaction may be carried out in an inert, polar organic solvent, for example methylene chloride, at room temperature, and the desired end product isolated in the usual manner and purified if desired. The keto group can if desired be converted into a functional derivative in the usual manner.

The following compounds are representative of those compounds of the formula II which can be used as starting material in the process of the present invention:

2-(4-chlorophenoxy)-1-hydroxy-4,4-dimethyl-pentan-3-one, 2-(2,4,5-trichlorophenoxy)-1-hydroxy-4,4-dimethyl-pentan-3-one, 2-(3-chlorophenoxy)-1-hydroxy-4,4-dimethyl-pentan-3-one, 2-(3-chloro-4-methylphenoxy)-1-hydroxy-4,4-dimethyl-pentan-3-one,
2-(3-trifluoromethylphenoxy)-1-hydroxy-4,4-dimethyl-pentan-3-one,
2-phenoxy-1-hydroxy-4,4-dimethyl-pentan-3-one,
2-(2,3-dimethylphenoxy)-1-hydroxy-4,4-dimethyl-pentan-3-one,
2-(2,3-dimethylphenoxy)-1-hydroxy-butan-3-one,
2-(2,3-dichlorophenoxy)-1-hydroxy-3-phenyl-propan-3-one,
2-(3,4-dichlorophenoxy)-1-hydroxy-3-phenyl-propan-3-one,
2-(4-chlorobenzyloxy)-1-hydroxy-4,4-dimethyl-pentan-3-one,
2-(4-chlorophenoxy)-1-chloro-4,4-dimethyl-pentan-3-one,
2-(4-methylphenoxy)-1-chloro-4,4-dimethyl-pentan-3-one,
2-(3-chlorphenoxy)-1-chloro-4,4-dimethyl-pentan-3-one,
2-(2-chlorophenoxy)-1-chloro-4,4-dimethyl-pentan-3-one,
2-(phenoxy)-1-chloro-4,4-dimethyl-pentan-3-one,
2-(2-methylphhenoxy)-1-chloro-4,4-dimethyl-pentan-3-one,
2-(2,3-dimethylphenoxy)-1-chloro-4,4-dimethyl-pentan-3-one,
2-(2,4-dimethylphenoxy)-1-chloro-4,4-dimethyl-pentan-3-one,
2-(3,4-dimethylphenoxy)-1-chloro-4,4-dimethyl-pentan-3-one,
2-(3-trifluoromethylphenoxy)-1-chloro-4,4-dimethyl-pentan-3-one,
2-(3-trifluoromethylphenoxy)-1-chloro-3-phenyl-propan-3-one,
2-(3-trifluoromethylphenoxy)-1-chloro-4-phenyl-butan-3-one,
2-(2-chlorobenzyloxy)-1-chloro-4-phenyl-butan-3-one,
2-(2-chlorobenzyloxy)-1-chloro-4,4-dimethyl-pentan-3-one,
2-(4-methylbenzyloxy)-1-chloro-4,4-dimethyl-pentan-3-one, and
2-(3,4-dimethylphenoxy)-1-chloro-3-phenyl-propan-3-one.

The halogen compounds of the formula III used as starting compounds in Process Variant (b) are not known but can be produced by conventional methods. They can be obtained, for example, by reacting alcohols or thiols of the general formula:

$$R^2YH \qquad IV,$$

wherein $R^2$ and Y are as above defined, in the usual manner with a halogenoketone of the formula:

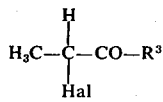

$$V,$$

wherein $R^3$ and Hal are as defined above. Hal is preferably chlorine or bromine. The active hydrogen atom in the α-position is subsequently replaced by halogen in the customary manner, for example by means of elementary bromine in carbon tetrachloride at 40° to 50° C, and the keto group is converted if desired into a functional derivative in the customary manner. The desired product is isolated in a known manner and is purified if desired.

The following compounds are illustrative of the compounds of the formula III which can be used as starting materials according the process of the present invention:
2-(4-chlorophenoxy)-2-bromo-4,4-dimethylpentan-3-one,
2-(2,4-dichlorophenoxy)-2-bromo-4,4-dimethylpentan-3-one,
2-(4-bromophenoxy)-2-bromo-4,4-dimethylpentan-3-one,
2-(2-diphenoxy)-2-bromo-4,4-dimethylpentan-3-one,
2-(4-fluorophenoxy)-2-bromo-4,4-dimethylpentan-3-one,
2-(2-chlorophenoxy)-2-bromo-4,4-dimethylpentan-3-one,
2-(4-methylphenoxy)-2-bromo-4,4-dimethylpentan-3-one,
2-(3-chlorophenoxy)-2-bromo-4,4-dimethylpentan-3-one,
2-(2,4,5-trichlorophenoxy)-2-bromo-4,4-dimethyl-pentan-3-one,
2-(3,4-dimethylphenoxy)-2-bromo-4,4-dimethylpentan-3-one,
2-(2,3-dimethylphenoxy)-2-bromo-4,4-dimethylpentan-3-one and
2-(2,4-dimethylphenoxy)-2-bromo-4,4-dimethylpentan-3-one.

As diluent in Process Variant (a), when $R^4$ is hydroxy (reaction of the β-hydroxy compounds of the formula II with imidazole), there may be used any inert, higher-boiling, water-immiscible organic solvents. Preferred solvents include aliphatic and aromatic hydrocarbons boiling about 50° C, such as ligroin, benzene and toluene.

The reaction of Process Variant (a) when $R^4$ is hydroxy is preferably carried out in the presence of a dehydrating agent, such as calcined calcium carbonate or dry sodium sulphate, or with the aid of a water-separator.

In Process Variant (a), when $R^4$ is hydroxy, the reaction temperatures can be varied over a substantial range. In general, the reaction is carried out at between 50° and 180° C, and preferably at 80° to 140° C.

In carrying out Process Variant (a) according to the invention, when $R^4$ is hydroxy, preferably 1 to 5, especially 1 to 1.5, mols of imidazole, and 0.5 to 20, especially 1 to 5, mols of the dehydrating agent (if used) are generally employed per 1 mol of the compound of the formula II.

The isolation of the compounds of the general formula I can be carried out according to generally known, customary methods. For example, the solvent can be distilled off in vacuo and the residue taken up with methylene chloride and water. The organic phase is subsequently separated off. After drying over sodium sulphate, the solvent is distilled off in vacuo. The resulting residue is purified by recrystallization. If purification by recrystallization does not suffice, it is possible, after distilling off the solvent for the first time, to prepare a salt and to purify this by recrystallization. The 1-ethyl-imidazole of the formula I can be liberated in the form of the free base from the salt in a known manner, by adding a strong base.

As diluent in Process Variant (a), when $R^4$ is chlorine or bromine (reaction of the β-halogen compounds of the general formula II with imidazole) there may be used any polar organic solvent which is inert towards the process according to the invention. Preferred solvents include ethers (especially cyclic ethers such as dioxane or tetrahydrofurane), nitriles (especially lower alkylnitriles, such as acetonitrile), amides (especially lower dialkylamides, such as dimethylformamide) and sulphoxides (especially lower dialkylsulphoxides, such as dimethylsulphoxide).

The reaction in Process Variant (a) when $R^4$ is chlorine or bromine is preferably carried out in the presence of an acid-binding agent. Appropriately, a suitable excess of imidazole is used. However, it is also possible to employ any of the conventional organic acid-binding agents, such as lower tertiary alkylamines (for example triethylamine) or secondary organic bases (for example pyridine).

In Process Variant (a), when $R^4$ is chlorine or bromine, the reaction temperatures can be varied over a substantial range. In general the reaction is carried out at between 50° and 150°, preferably at 80° C to 150° C.

In carrying out the Process Variant (a) according to the invention, when $R^4$ is chlorine or bromine, preferably 1 to 5, preferably 1 to 1.5, mols of imidazole and additionally 1 to 10, preferably 1 to 2, mols of the acid-binding agent (for example imidazole) are employed per 1 mol of the compound of the general formula II.

The isolation and purification is carried out according to generally known methods, for example in the manner indicated above (for Process Variant (a) when $R^4$ is hydroxy).

As diluent in Process Variant (b) (reaction of the α-halogenoether compounds of the general formula III with imidazole) there may be used any inert, preferably polar, organic solvent. Suitable solvents include nitriles (especially lower alkylnitriles, such as acetonitrile), sulphoxides (especially lower dialkylsulphoxides, such as dimethylsulphoxide), formamides (especially lower dialkylformamides such as dimethylformamide), ketones (especially lower dialkyl ketones, such as acetone), straight-chain and cyclic ethers (such as diethyl ether and tetrahydrofurane), and chlorinated hydrocarbons (such as methylene chloride and chloroform).

Any of the customary acid-binding agents can be used as acid-binding agent in Process Variant (b). Preferred acid-binding agents include organic acid-binding agent (such as lower tertiary alkylamines) and aralkylamines (for example triethylamine and dimethylbenzylamine). Preferably, excess imidazole is employed as the acid-binding agent.

In Process Variant (b), the reaction temperatures can be varied over a substantial range. In general, the reaction is carried out between 20° and 150° C, preferably at 60° to 120° C.

In carrying out the Process Variant (b) according to the invention, preferably 1 to 5, especially 1 to 1.5, mols of imidazole and additionally preferably 1 to 10, especially 1 to 2, mols of the acid-binding agent (for example imidazole) are employed per 1 mol of the compound of the general formula III.

The compounds of the general formula I can be isolated and purified according to generally known methods, for example in the manner indicated above (for Process Variant (a) when $R^4$ is hydroxy).

The free 1-ethyl imidazole bases of formula I and their salts can be interconverted in any suitable manner. Methods for such interconversion are known in the art. For example, the free 1-ethyl imidazole base can be dissolved in an organic solvent, for example diethyl ether, and treated with the acid, for example hydrohalic acid. The salt precipitates and is filtered off or is obtained as a residue by distilling off the solvent.

The following compounds are representative of the 1-ethyl-imidazoles of the present invention:

2-(4-chlorophenoxy)-1-imidazolyl-(1)-4,4-dimethyl-pentan-3-one, 2-(2,4,5-trichlorophenoxy)-1-imidazolyl-(1)-4,4-dimethyl-pentan-3-one, 2-(3-chlorophenoxy)-1-imidazolyl-(1)-4,4-dimethyl-pentan-3-one, 2-(3-chloro-4-methylphenoxy)-1-imidazolyl-(1)-4,4-dimethyl-pentan-3-one, 2-(3-trifluoromethyl-phenoxy)-1-imidazolyl-(1)-4,4-dimethyl-pentan-3-one, 2-phenoxy-1-imidazolyl-(1)-4,4-dimethyl-pentan-3-one, 2-(2,3-dimethylphenoxy)-1-imidazolyl-(1)-4,4-dimethylpentan-3-one, 2-(2,3-dimethylphenoxy)-1-imidazolyl-(1)-butan-3-one, 2-(2,3-dichlorophenoxy)-1-imidazolyl-(1)-3-phenyl-propan-3-one, 2-(3,4-dichlorophenoxy)-1-imidazolyl-(1)-3-phenyl-propan-3-one, 2-(4-chlorobenzyloxy)-1-imidazolyl-(1)-4,4-dimethyl-pentan-3-one, 2-(4-methoxyphenoxy)-1-imidazolyl-(1)-4,4-dimethyl-pentan-3-one, 2-(4-methylphenoxy)-1-imidazolyl-(1)-4,4-dimethyl-pentan-3-one, 2-(3-nitrophenoxy)-1-imidazolyl-(1)-4,4-dimethyl-pentan-3-one, 2-(2-chlorophenoxy)-1-imidazolyl-(1)-4,4-dimethyl-pentan-3-one, 2-(phenoxy)-1-imidazolyl-(1)-4-ethyl-4-methyl-pentan-3-one, 2-(3-methylphenoxy)-1-imidazolyl-(1)-4,4-dimethyl-pentan-3-one, 2-(2-chloro-3-methylphenoxy)-1-imidazolyl-(1)-4,4-dimethyl-pentan-3-one, 2-(2,4-dimethylphenoxy)-1-imidazolyl-(1)-4,4-dimethyl-pentan-3-one, 2-(3,4-dimethylphenoxy)-1-imidazolyl-(1)-4,4-dimethyl-pentan-3-one, 2-(3-cyanophenoxy)-1-imidazolyl-(1)-4-ethyl-4-methyl-pentan-3-one, 2-(3-trifluoromethylphenoxy)-1-imidazolyl-(1)-3-phenyl-propan-3-one, 2-(3-trifluoromethylphenoxy)-1-imidazolyl-(1)-4-phenyl-butan-3-one, 2-(2-chlorobenzyloxy)-1-imidazolyl-(1)-4-phenyl-butan-3-one, 2-(2-chlorobenzyloxy)-1-imidazolyl-(1)-4,4-dimethyl-pentan-3-one, 2-(4-methylbenzyloxy)-1-imidazolyl-(1)-4,4-dimethyl-pentan-3-one, 2-(3,4-dimethylphenoxy)-1-imidazolyl-(1)-3-phenyl-propan-3-one, 2-(4-methylthiophenoxy)-1-imidazolyl-(1)-4,4-dimethyl-pentan-3-one, 2-(2,4-dichlorophenoxy)-1-imidazolyl-(1)-4,4-dimethyl-pentan-3-one, 2-(4-bromophenoxy)-1-imidazolyl-(1)-4,4-dimethyl-pentan-3-one, 2-(4-fluorophenoxy)-1-imidazolyl-(1)-4,4-dimethyl-pentan-3-one, 2-(2-chloro-4-methylphenoxy)-1-imidazolyl-(1)-4,4-dimethyl-pentan-3-one, 2-(4-nitrophenoxy)-1-imidazolyl-(1)-4,4-dimethyl-pentan-3-one, 2-(4-phenylphenoxy)-1-imidazolyl-(1)-4,4-dimethyl-pentan-3-one, 2-(2,4,5-tribromophenoxy)-1-imidazolyl-(1)-4,4-dimethyl-pentan-3-one, 2-(3,4-dimethoxyphenoxy)-1-imidazolyl-(1)-4,4-dimethyl-pentan-3-one, 2-(2-phenylphenoxy)-1-imidazolyl-(1)-4,4-dimethyl-pentan-3-one, and 2-(2-fluoro-4-methylphenoxy)-1-imidazolyl-(1)-4,4-dimethyl-pentan-3-one.

The compounds according to the present invention exhibit very good and broad antimycotic activity, especially against dermatophytes, epidermatophytes and blastomyces as well as against biphase fungi and yeast fungi, for example *Trichophyton* and *Candida*. They can therefore be employed successfully against fungal infections in humans and animals.

Examples of fields of indication in human medicine include:

Dermatomycoses and systemic mycoses due to *Trichophyton mentagrophytes* and other varieties of *Trichophyton*, varieties of *Microsporon*, *Epidermophyton floccosum*, blastomyces, biphase fungi, and molds.

Examples of fields of indication in veterinary medicine include:

All dermatomycoses and systemic mycoses, especially those caused by the above-mentioned pathogens.

The present invention also includes pharmaceutical compositions which comprise a 1-ethyl-imidazole as hereinabove described as the active ingredient in combination with a pharmaceutically acceptable, nontoxic, inert diluent or carrier.

The pharmaceutical compositions of the present invention contain a major or minor amount, e.g. 99.5% to 0.1%, preferably 95% to 0.5%, of at least 1-ethyl-imidazole of the present invention in combination with a pharmaceutically acceptable, nontoxic, inert diluent or carrier, the carrier comprising one or more solid, semisolid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, 3 or 4 times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 30 to 200, and preferably 50 to 200, mg/kg of body weight per day. In some instances a sufficient therapeutic effect can be obtained at a lower dose while in others, a larger dose will be required.

Oral administration can be effected utilizing solid and liquid dosage unit forms such as powders, tablets dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be graunlated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginuos medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred dialy dose is 1.5 to 18.0 g. preferably 2.5 to 18.0 g, of active agent.

While the routes of administration include oral, parenteral (i.e., intramuscular, intraperitoneal, and intravenous), rectal, and topical, oral administration and topical application are particularly preferred.

The antimycotic activity of representative compounds according to the present invention is demonstrated from the following in vitro and in vivo experimental data:

Determination of the anti-mycotic action spectrum in vitro by the series dilution test.

Description of the test:

The nutrient substrates used were, for dermatophytes and moulds, Sabourauds' test medium, and, for blastomyces and biphase fungi, meat broth-glucose bouillon.

The incubation temperature was 28°C and the incubation time was 24 to 96 hours.

The experimental results are summarized in Table A.

Table A:

| Compound from Example No. | Minimum inhibitory concentration values in γ/ml of nutrient medium | | | | |
|---|---|---|---|---|---|
| | Active compound | Trichophyton mentagrophytes | Candida albicans | Penicillium commune | Aspergillus niger |
| 1 | [imidazole-$CH_2$-CH-O-C$_6$H$_4$-Cl with CO-C($CH_3$)$_3$] | 4 | 4 | 32 | 8 |
| 4 (Hydrochloride) | [imidazole-$CH_2$-C(H)-O-C$_6$H$_4$-Cl with CO-C($CH_3$)$_3$] · HCl | 4 | 4 | 32 | 4 |
| 5 | [imidazole-$CH_2$-CH-O-C$_6$H$_3$Cl$_2$ with CO-C($CH_3$)$_3$] · HCl | <1 | 4 | 16 | 4 |
| 6 | [imidazole-$CH_2$-CH-O-C$_6$H$_4$-Br with CO-C($CH_3$)$_3$] · HCl | 8 | 4 | 16 | 4 |

Table A:-continued
Minimum inhibitory concentration values in γ/ml of nutrient medium
| Compound from Example No. | Active compound | Trichophyton mentagrophytes | Candida albicans | Penicillium commune | Aspergillus niger |
|---|---|---|---|---|---|
| 13 | 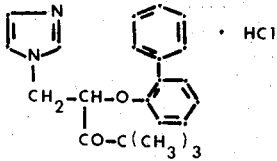 | 8 | 4 | 16 | 8 |
| 7 | 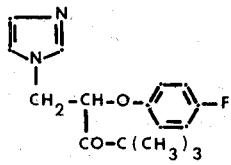 | 8 | 4 | 32 | 4 |
| 8 | 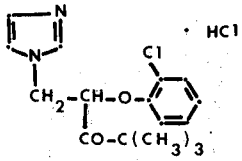 | 8 | 4 | 16 | 4 |
| 12 | 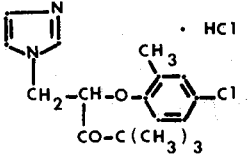 | <1 | 4 | 8 | 8 |
| 14 | 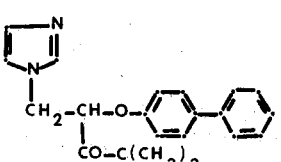 | <1 | 4 | 8 | 8 |
| 15 | 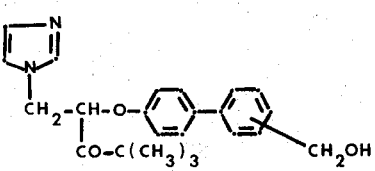 | <1 | 4 | 8 | 4 |

Table A:-continued

| Compound from Example No. | Active compound | Minimum inhibitory concentration values in γ/ml of nutrient medium | | | |
|---|---|---|---|---|---|
| | | Trichophyton mentagrophytes | Candida albicans | Penicillium commune | Aspergillus niger |
| 10 | [imidazole-CH₂-CH(O-2,4,6-trichlorophenyl)-CO-C(CH₃)₃ · HCl] | 4 | 4 | 16 | 4 |
| 9 | [imidazole-CH₂-CH(O-2-chlorophenyl)-CO-C(CH₃)₃ · HCl] | 4 | 4 | 16 | 4 |

Anti-mycotic action of the compounds according to the invention, in animal experiments.

a. Topical application in experimental guinea pig trichophytosis (pathogen: *Trichophyton mentagrophytes*)

Description of the experiment:

A 1% strength solution of the active compounds in a dimethylsulphoxide/glycerine/water mixture (1 : 3 : 6) or in polyethylene glycol 400 was applied topically once daily for 11 to 14 days, after the trichophytosis had been initiated experimentally.

The experimental results are reproduced in Table B:

Table B:

Action of the compounds according to the invention, of the formula I, in guinea pig trichophytosis

| Compound from Example No. | Topical action in the case of Trichophyton mentagrophytes |
|---|---|
| 1 | +++ |
| 4 | +++ |
| 5 | +++ |
| 6 | +++ |
| 13 | ++ |
| 7 | +++ |
| 8 | +++ |
| 12 | +++ |
| 14 | +++ |
| 10 | ++++ |
| 9 | +++ |

| ++ = weak action | (reduction of the infection symptoms) |
| +++ = action | (rapid healing of the infection) |
| ++++ = good action | (complete suppression of the infection symptoms) |
| +++++ = very good action | | b. Action (oral administration) in Quinckeanum trichophytosis of white mice

The development of the Quinckeanum infection in mice could be suppressed with doses of 2 × 100 mg/kg of body weight, given orally once daily up to the eighth day of the infection.

The result can be seen from Table C:

Table C:

Action of the compounds according to the invention, of the formula I, in the case of *Quinckeanum* trichophytosis of white mice.

| Compound from Example No. | Oral action in the case of Trichophyton quinckeanum |
|---|---|
| 1 | ++++ |
| 4 | ++++ |
| 5 | +++ |
| 6 | +++ |
| 7 | ++++ |
| 8 | +++ |
| 12 | +++ |
| 14 | +++ |
| 9 | +++ |

Explanation of symbols: see Table B c. Candidosis of mice

Description of the experiment:

Mice of type SPF-CF$_1$ were infected intravenously with $1 - 2 \times 10^6$ of logarithmically growing Candida cells suspended in physiological sodium chloride solution.

The animals were treated orally twice daily, after infection, with 100 mg of the preparations/kg of body weight.

Untreated animals died of the infection 3 to 6 days after infection. The survival rate on the 6th day after infection was 2 to 3 per 20 animals (i.e. 10 – 15%) in the case of the control animals.

The experimental results are summarized in Table D:

Table D:

| Compound from Example No: | Action (on oral administration) in candidosis of mice Action on *Candida albicans* |
|---|---|
| 1 | +++++ |
| 4 | ++++ |
| 5 | ++++ |
| 6 | ++++ |
| 7 | +++++ |
| 8 | +++ |
| 12 | +++ |
| 14 | +++ |
| 15 | ++ |
| 9 | ++++ |

Explanation of symbols:
++++ = good action = >80% surviving on the 6th day after infection.
+++++ = very good action = >90% surviving on the 6th day after infection.

The following non-limitative examples more particularly illustrate the present invention:

EXAMPLE 1

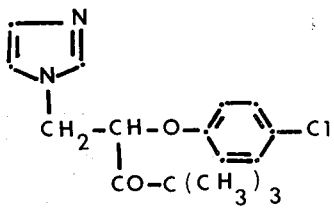

16.0 g (0.05 mol) of 2-(4-chlorophenoxy)-2-bromo-4,4-dimethyl-pentan-3-one in 120 ml of acetonitrile are heated to the boil under reflux for 12 hours, with 12 g (0.207 mol) of imidazole. The solvent is then distilled off in vacuo, almost to dryness, and thereafter 50 ml of ether and 50 ml of saturated solution of hydrogen chloride in ether are added. The resulting oil is decanted and boiled up three times with 50 ml of ether at a time, and the ether phase is decanted.

The oil which remains is taken up with 120 ml of methylene chloride; this is mixed with 50 ml of water, 20 g of solid sodium bicarbonate are added, the organic phase is separated off and the aqueous phase is extracted twice with 50 ml of methylene chloride at a time. The combined organic phases are washed twice with 50 ml of water at a time, dried over sodium sulphate and distilled off in vacuo. The resulting oil is triturated with ligroin/petroleum ether, whereupon it crystallizes. After recrystallization from ligroin/petroleum ether, 2.6 g of 2-(4-chlorophenoxy)-1-imidazolyl-(1)-4,4-dimethyl-pentan-3-one (17% of theory) of melting point 68°–73°C are obtained.

| NMR: | $\zeta$ CH | 5.18 (Triplet) |
|---|---|---|
|  | $\zeta$ CH$_2$ | 4.40 (Doublet) |

Starting compound

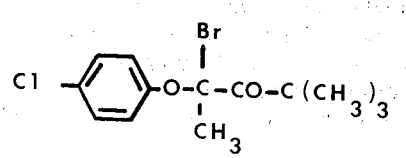

The starting product, 2-(4-chlorophenoxy)-2-bromo-4,4-dimethyl-pentan-3-one, is obtained by bromination of 2-(4-chlorophenoxy)-4,4-dimethyl-pentan-3-one with elementary bromine in carbon tetrachloride at 40°–50°C; melting point 95°C.

The remaining starting compounds are obtainable in the same manner.

Example 2

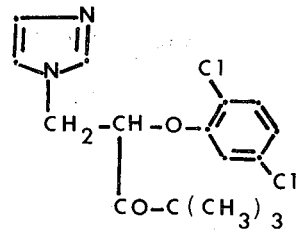

29.1 g (0.1 mol) of 2-(2,5-dichlorophenoxy)-1-hydroxy-4,4-dimethyl-pentan-3-one are taken up in 200 ml of toluene, 10.2 g (0.14 mol) of imidazole is added thereto and the reaction solution is boiled for 3 hours under a water separator. Thereafter the solvent is distilled off in vacuo, 100 ml of water are added to the oil obtained and the mixture is extracted twice with 100 ml of methylene chloride at a time.

The organic phase is washed with twice 50 ml of water and dried over sodium sulphate an the solvent is distilled off in vacuo.

An oil is obtained which is taken up in 50 ml of ether and treated with 50 ml of ether saturated with dry hydrogen chloride. The solvent is distilled off in vacuo and the resulting oil is taken up in a mixture of 500 ml of ligroin and 300 ml of ethyl acetate and heated to the boil under reflux. After carefully decanting the resulting solution and cooling it, 18.5 g (49% of theory) of 2-(2,5-dichlorophenoxy)-4,4-dimethyl-1-(1-imidazolyl)-pentan-3-one hydrochloride precipitate as colorless crystals which are isolated by filtration.

Melting point: 162°C (decomposition)

Starting compound

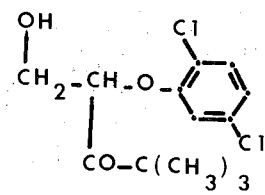

26.1 g (0.1 mol) of 1-(2,5-dichlorophenoxy)-3,3-dimethyl-butan-2-one are dissolved in 200 ml of ethanol and 20 g (0.24 mol) of 40% strength formaldehyde solution are added thereto, followed by about 5 ml of 10% strength sodium hydroxide solution until pH 9 is reached. The reaction mixture is heated under reflux for 3 hours and the solvent is distilled off in vacuo. The resulting precipitate is filtered off and well rinsed with petroleum ether. The filtrate is concentrated in vacuo. An oil remains: Crude 2-(2,5-dichlorophenoxy)-1-hydroxy-4,4-dimethyl-pentan-3-one.

The remaining starting compounds are obtainable in the same manner. In many cases, the compounds of the general formulae IV and V can be reacted with imidazole under the above-mentioned conditions, in a one-pot process, via the compounds of the general formula II, to give the compounds of the formula I.

Example 3

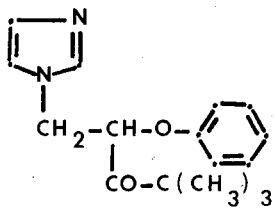

24 g (0.1 mol) of 1-chloro-2-phenoxy-4,4-dimethyl-pentan-3-one of refractive index $n_D^{20} = 1.5081$ are added to a solution of 13.6 g (0.2 mol) of imidazole in 150 ml of anhydrous acetonitrile. The resulting solution is heated for 4 hours to the boil under reflux; thereafter the solvent is distilled off in vacuo. The residue is washed with water and taken up in methylene chloride and the solution is dried over sodium sulphate. After distilling off the solvent, 25.3 g (93% of theory) of 1-imidazolyl-(1)-2-phenoxy-4,4-dimethyl-pentan-3-one are obtained as an oil of refractive index $n_D^{20} = 1.5193$, which gradually crystallizes and then possesses a melting point of 73°–75°C (recrystallized from petroleum ether).

Starting compound

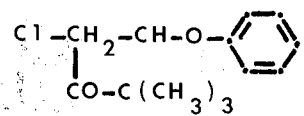

22.3 g (0.1 mol) of 1-hydroxy-2-phenoxy-4,4-dimethyl-pentan-3-one (produced as described in Example 2) are dissolved in 120 ml of methylene chloride and 7.3 ml (0.1 mol) of thionyl chloride are added dropwise to this solution at room temperature. The start of the reaction can be accelerated by gentle warming. After three hours' reaction time at room temperature the solvent is distilled off in vacuo and the oily residue is degassed in a high vacuum.

21.8 g (91% of theory) of 1-chloro-2-phenoxy-4,4-dimethyl-pentan-3-one are obtained as an oil of refractive index $n_D^{20} = 1.5081$.

The remaining starting compounds can be obtained in the same manner.

Examples 4 through 19 set forth in Table 1 below are obtained according to Process Variants (a) and (b) according to the processes set forth in Examples 1 to 3 above utilizing the corresponding reactants set forth in Table 2.

Table 1

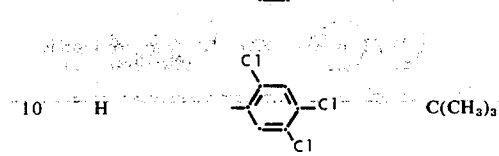

| Example No. | R¹ | R² | R³ | X | Y | Melting point °C |
|---|---|---|---|---|---|---|
| 4 | H | -⟨⟩-Cl | C(CH₃)₃ | CO | O | Hydrochloride 127 |
| 5 | H | -⟨⟩-Cl (Cl) | C(CH₃)₃ | CO | O | Hydrochloride 118 free Base 85–87 |
| 6 | H | -⟨⟩-Br | C(CH₃)₃ | CO | O | Hydrochloride 148–150 |
| 7 | H | -⟨⟩-F | C(CH₃)₃ | CO | O | 102–106 |
| 8 | H | -⟨⟩ (Cl) | C(CH₃)₃ | CO | O | Hydrochloride 146–148 free Base 77–79 |
| 9 | H | -⟨⟩ (Cl) | C(CH₃)₃ | CO | O | Hydrochloride 82–90 free Base 80–82 |
| 10 | H | -⟨⟩-Cl (Cl, Cl) | C(CH₃)₃ | CO | O | Hydrochloride 180–183 |

Table 1-continued

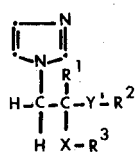

| Example No. | R¹ | R² | R³ | X | Y | Melting point °C |
|---|---|---|---|---|---|---|
| 11 | H | (4-methylphenyl) | C(CH₃)₃ | CO | O | Hydrochloride 135 |
| 12 | H | (Cl, CH₃-phenyl) | C(CH₃)₃ | CO | O | Hydrochloride 147–150 free Base 49–51 |
| 13 | H | (naphthyl) | C(CH₃)₃ | CO | O | Hydrochloride 144–146 |
| 14 | H | (biphenyl) | C(CH₃)₃ | CO | O | 111–112 |
| 15 | H | (biphenyl-CH₂OH)* | C(CH₃)₃ | CO | O | 105–107 |
| 16 | H | (2,6-dimethylphenyl) | C(CH₃)₃ | CO | O | Hydrochloride 143–147 free Base 97–98 |
| 17 | H | (2,6-dimethylphenyl, isomer) | C(CH₃)₃ | CO | O | Hydrochloride 164–165 |
| 18 | H | (3,5-dimethylphenyl) | C(CH₃)₃ | CO | O | Hydrochloride 157 |
| 19 | H | (4-O₂N-phenyl) | C(CH₃)₃ | CO | O | 119–120 |
| 20 | H | (O₂N, Cl-phenyl) | C(CH₃)₃ | CO | O | 122–123 |
| 21 | H | (Cl-phenyl) | (cyclohexyl) | CO | O | Hydrochloride 148–150 |

\* Position of the CH₂OH group not known.

Table 2

| Example No. | Reactants |
|---|---|
| Imidazole is reacted with: | |
| 4 | 1-hydroxy-2-(4-chlor-phenoxy)-4,4-dimethyl-pentan-3-one |
| 5 | 1-hydroxy-2-(2,4-dichlor-phenoxy)-4,4-dimethyl-pentan-3-one |
| 6 | 1-hydroxy-2-(4-brom-phenoxy)-4,4-dimethyl-pentan-3-one |
| 7 | 1-hydroxy-2-(4-fluor-phenoxy)-4,4-dimethyl-pentan-3-one |
| 8 | 1-hydroxy-2-(2-chlor-phenoxy)-4,4-dimethyl-pentan-3-one |
| 9 | 1-hydroxy-2-(3-chlor-phenoxy)-4,4-dimethyl-pentan-3-one |
| 10 | 1-hydroxy-2-(2,4,5-trichlor-phenoxy)-4,4-dimethyl-pentan-3-one |
| 11 | 1-hydroxy-2-(4-methyl-phenoxy)-4,4-dimethyl-pentan-3-one |
| 12 | 1-hydroxy-2-(2-methyl-4-chlor-phenoxy)-4,4-dimethyl-pentan-3-on |
| 13 | 1-hydroxy-2-(2-phenyl-phenoxy)-4,4-dimethyl-pentan-3-one |
| 14 | 1-hydroxy-2-(4-phenyl-phenoxy)-4,4-dimethyl-pentan-3-one |
| 15 | 1-hydroxy-2-(4-phenyl-hydroxymethyl-phenoxy)-4,4-dimethyl-pentan-3-one |
| 16 | 1-hydroxy-2-(2,3-dimethyl-phenoxy)-4,4-dimethyl-pentan-3-one |
| 17 | 1-hydroxy-2-(3,4-dimethyl-phenoxy)-4,4-dimethyl-pentan-3-one |
| 18 | 1-hydroxy-2-(2,4-dimethyl-phenoxy)-4,4-dimethyl-pentan-3-one |
| 19 | 1-hydroxy-2-(4-nitrophenoxy)-4,4-dimethyl-pentan-3-one |
| 20 | 1-hydroxy-2-(2-chlor-4-nitro-phenoxy)-4,4-dimethyl-pentan-3-one |
| 21 | 1-hydroxy-2-(4-chlor-phenoxy)-3-cyclohexyl-propan-3-one |

What is claimed is:
1. A compound of the formula

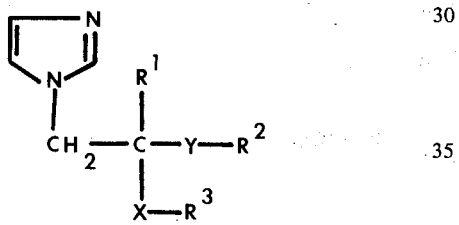

wherein
$R^1$ and $R^3$ are the same or different and are hydrogen, straight or branched-chain lower alkyl, straight or branched-chain lower alkenyl, cycloalkyl of 3 to 7 carbon atoms, cycloalkenyl of 5 to 7 carbon atoms, aryl of 6 to 10 carbon atoms unsubstituted or substituted by 1 to 3 of the same or different substituents selected from the group consisting of halogen, halogenoalkyl of 1 or 2 carbon atoms in the alkyl moiety and 2 to 5 halogen atoms, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethyl-substituted phenyl, or aralkyl of 6 to 10 carbon atoms in the aryl moiety and 1 to 4 carbon atoms in the alkyl moiety unsubstituted or substituted by 1 to 3 of the same or different substituents selected from the group consisting of halogen, halogenoalkyl of 1 or 2 carbon atoms in the alkyl moiety and 2 to 5 halogeno moieties, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl or hydroxymethyl-substituted phenyl;
$R^2$ is straight or branched-chain lower alkyl, straight or branched-chain lower alkynyl, cycloalkyl of 3 to 7 carbon atoms, cycloalkenyl of 5 to 7 carbon atoms, aryl of 6 to 10 carbon atoms unsubstituted or substituted by 1 to 3 of the same or different substituents selected from the group consisting of halogen, halogenoalkyl of 1 or 2 carbon atoms in the alkyl moiety and 2 to 5 halogeno moieties, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethyl-substituted phenyl, or aralkyl of 6 to 10 carbon atoms in the aryl moiety and 1 to 4 carbon atoms in the alkyl moiety unsubstituted or substituted by 1 to 3 of the same or different substituents selected from the group consisting of halogen, halogenoalkyl of 1 or 2 carbon atoms in the alkyl moiety and 2 or 5 halogen moieties, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethyl-substituted phenyl;
X is C=O; and
Y is oxygen or sulphur;
or a pharmaceutically acceptable nontoxic salt thereof.
2. A compound according to claim 1 wherein
$R^1$ is hydrogen;
$R^2$ is phenyl unsubstituted or substituted by 1 to 3 members selected from the group consisting of fluorine, chlorine, bromine, alkyl of 1 to 4 carbon atoms, alkoxy of 1 to 4 carbon atoms, trifluoromethyl, nitro, cyano and thioalkyl of 1 to 4 carbon atoms, or by 1 member selected from the group consisting of phenyl and hydroxymethyl-substituted phenyl, or benzyl unsubstituted or substituted by chlorine, bromine, fluorine or methyl;
$R^3$ is lower alkyl, phenyl, benzyl or cyclohexyl;
X is C=O; and
Y is oxygen.
3. A compound according to claim 1 wherein
$R^1$ is hydrogen;
$R^2$ is phenyl unsubstituted or substituted by 1 to 3 members selected from the group consisting of chlorine, bromine and fluorine, by 1 member selected from the group consisting of chlorine bromine and fluorine and 1 alkyl moiety of 1 to 4 carbon atoms, by 1 or 2 members selected from the group consisting of alkyl of 1 to 4 carbon atoms, alkoxy of 1 to 4 carbon atoms, trifluoromethyl, thioalkyl of 1 to 4 carbon atoms, nitro, and cyano, or by phenyl or hydroxymethyl-substituted phenyl, or benzyl unsubstituted or substituted by chlorine or methyl;

$R^3$ is alkyl of 1 to 5 carbon atoms, phenyl, benzyl or cyclohexyl;

X is C=O; and

Y is oxygen.

4. A compound according to claim 1 wherein
$R^1$ is hydrogen;
$R^2$ is phenyl unsubstituted or substituted by 1 to 3 chlorine, bromine or fluorine, by 1 chlorine, bromine or fluorine and 1 methyl group, by 1 or 2 methyl or methoxy groups, or by 1 methoxy, trifluoromethyl, nitro, cyano, thiomethyl, phenyl or hydroxymethyl-substituted phenyl, or benzyl unsubstituted or substituted by chlorine or methyl;
$R^3$ is methyl, tert.-butyl, pentyl, phenyl or benzyl;
X is C=O; and
Y is oxygen.

5. A compound according to claim 1 in the form of a salt wherein said salt is selected from the group consisting of the hydrochloride, the hydrobromide, the phosphate, the nitrate, the acetate, the maleate, the succinate, the fumarate, the tartrate, the citrate, the salicylate, the sorbate, the lactate and the 1,5-naphthalene disulphonate.

6. The compound according to claim 1 which is

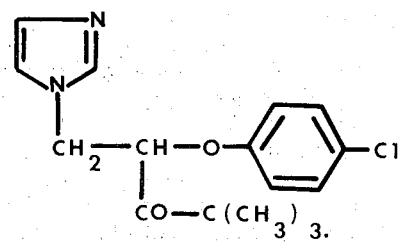

7. The compound according to claim 1 which is

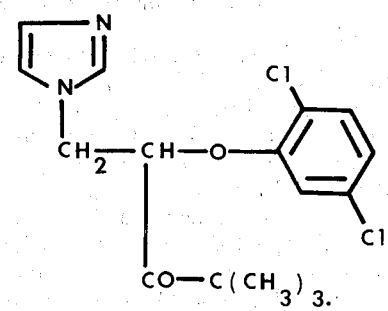

8. The compound according to claim 1 which is

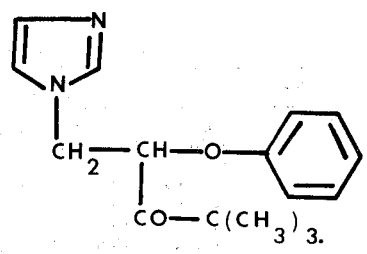

9. A compound according to claim 1 wherein
$R^1$ is hydrogen;
$R^2$ is

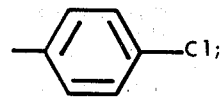

$R^3$ is $C(CH_3)_3$;
X is CO; and
Y is oxygen;
or the hydrochloride salt thereof.

10. A compound according to claim 1 wherein
$R^1$ is hydrogen;
$R^2$ is

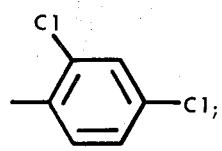

$R^3$ is $C(CH_3)_3$;
X is CO; and
Y is oxygen;
or the hydrochloride salt thereof.

11. A compound according to claim 1 wherein
$R^1$ is hydrogen;
$R^2$ is

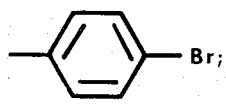

$R^3$ is $C(CH_3)_3$;
X is CO; and
Y is oxygen;
or the hydrochloride salt thereof.

12. A compound according to claim 1 wherein
$R^1$ is hydrogen;
$R^2$ is

13. A compound according to claim 1 wherein
R$^1$ is hydrogen;
R$^2$ is

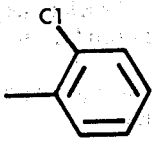

R$^3$ is C(CH$_3$)$_3$;
X is CO; and
Y is oxygen;
or the hydrochloride salt thereof.

14. A compound according to claim 1 wherein
R$^1$ is hydrogen;
R$^2$ is

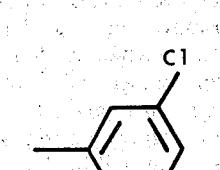

R$^3$ is C(CH$_3$)$_3$;
X is CO; and
Y is oxygen;
or the hydrochloride salt thereof.

15. A compound according to claim 1 wherein
R$^1$ is hydrogen;
R$^2$ is

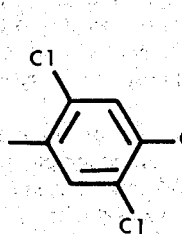

R$^3$ is C(CH$_3$)$_3$;
X is CO; and
Y is oxygen;
or the hydrochloride salt thereof.

16. A compound according to claim 1 wherein
R$^1$ is hydrogen;
R$^2$ is

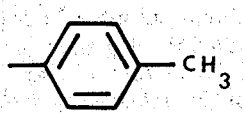

R$^3$ is C(CH$_3$)$_3$;
X is CO; and
Y is oxygen;
or the hydrochloride salt thereof.

17. A compound according to claim 1 wherein
R$^1$ is hydrogen;
R$^2$ is

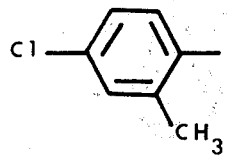

R$^3$ is C(CH$_3$)$_3$;
X is CO; and
Y is oxygen;
or the hydrochloride salt thereof.

18. A compound according to claim 1 wherein
R$^1$ is hydrogen;
R$^2$ is

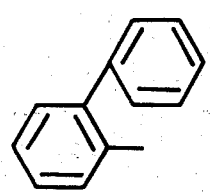

R$^3$ is C(CH$_3$)$_3$;
X is CO; and
Y is oxygen;
or the hydrochloride salt thereof.

19. A compound according to claim 1 wherein
R$^1$ is hydrogen;
R$^2$ is

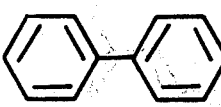

R$^3$ is C(CH$_3$)$_3$;
X is CO; and
Y is oxygen;
or the hydrochloride salt thereof.

20. A compound according to claim 1 wherein
R$^1$ is hydrogen;
R$^2$ is

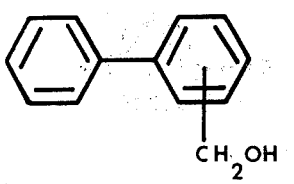

R³ is C(CH₃)₃;
X is CO; and
Y is oxygen;
or the hydrochloride salt thereof.

21. A compound according to claim 1 wherein
R¹ is hydrogen;
R² is

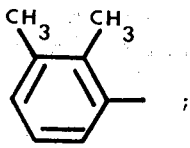

R³ is C(CH₃)₃;
X is CO; and
Y is oxygen;
or the hydrochloride salt thereof.

22. A compound according to claim 1 wherein
R¹ is hydrogen;
R² is

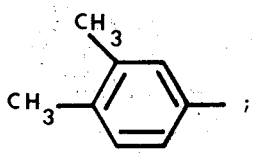

R³ is C(CH₃)₃;
X is CO; and
Y is oxygen;
or the hydrochloride salt thereof.

23. A compound according to claim 1 wherein
R¹ is hydrogen;
R² is

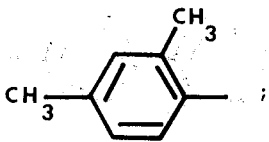

R³ is C(CH₃)₃;
X is CO; and
Y is oxygen;
or the hydrochloride salt thereof.

24. A compound according to claim 1 wherein
R¹ is hydrogen;
R² is

R³ is

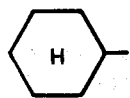

X is CO; and
Y is oxygen; or the hydrochloride salt thereof.

25. A process for the production of a compound of claim 1 wherein
R¹ is hydrogen; which comprises reacting a compound of the formula

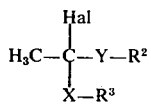

wherein
R² is a straight or branched-chain lower alkyl, straight or branched-chain lower alkynyl, cycloalkyl of 3 to 7 carbon atoms, cycloalkenyl of 5 to 7 carbon atoms, aryl of 6 to 10 carbon atoms unsubstituted or substituted by 1 to 3 of the same or different substituents selected from the group consisting of halogen, halogenoalkyl of 1 or 2 carbon atoms in the alkyl moiety and 2 to 5 halogeno moieties, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethyl-substituted phenyl, or aralkyl of 6 to 10 carbon atoms in the aryl moiety and 1 to 4 carbon atoms in the alkyl moiety unsubstituted or substituted by 1 to 3 of the same or different substituents selected from the group halogen, halogenoalkyl of 1 or 2 carbon atoms in the alkyl moiety and 2 or 5 halogeno moieties, straight or branched-chain alkyl of 1 to 4 carbon atoms, straight or branched-chain alkoxy of 1 to 4 carbon atoms, thioalkyl of 1 to 4 carbon atoms, alkyl sulphonyl of 1 to 4 carbon atoms, nitro, cyano, phenyl and hydroxymethyl-substituted phenyl;

R³ is hydrogen, straight or branched-chain lower alkyl, straight or branched-chain lower alkenyl cycloalkyl of 3 to 7 carbon atoms, cycloalkenyl of 5 to 7 carbon atoms, aryl of 6 to 10 carbon atoms unsubstituted or substituted by 1 to 3 of the same or different substituents selected from the group consisting of halogen, halogenoalkyl of 1 or 2 carbon atoms in the alkyl moiety and 2 to 5 halogen atoms, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethyl-substituted phenyl, or aralkyl of 6 to 10 carbon atoms in the aryl moiety and 1 to 4 carbon atoms in the alkyl moiety unsubstituted or substituted by 1 to 3 of the same or different substituents selected from the group consisting of halogen, halogenoalkyl of 1 or 2 carbon atoms in the alkyl moiety and 2 to 5 halogeno moieties, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl or hydroxymethyl-substituted phenyl;

X is C=O; and

Y is oxygen or sulphur;

Hal is halogen;

with imidazole in the presence of an acid binding agent at a temperature of from about 20° C to about 150° C, and, in the case of the salts, reacting the free base produced with the appropriate acid, and recovering the compound produced.

26. A process according to claim 25 wherein the reaction is carried out in the presence of an inert polar organic solvent.

27. A process according to claim 26 wherein the acid binding agent is an excess of imidazole.

28. A process according to claim 27 wherein the reaction temperature is from about 60° to about 150° C.

29. A process according to claim 28 wherein 1 to 5 mols of imidazole reactant and 1 to 10 mols of imidazole as acid-binding agent are used per mol of halide.

* * * * *

UNITED STATES PATENT AND TRADEMARK OFFICE
CERTIFICATE OF CORRECTION

PATENT NO. : 3,940,413
DATED : February 24, 1976
INVENTOR(S) : WOLFGANG KRAMER ET AL It is certified that error appears in the above-identified patent and that said Letters Patent are hereby corrected as shown below:

Columns 1 and 2 should read as follows:

The present invention is concerned with 1-ethyl-imidazoles, processes for their production, antimycotic compositions wherein said compounds are the active ingredient and methods of treating mycotic infections in humans and animals by administering such compounds to humans and animals.

More particularly the present invention is concerned with 1-ethyl-imidazoles of the formula

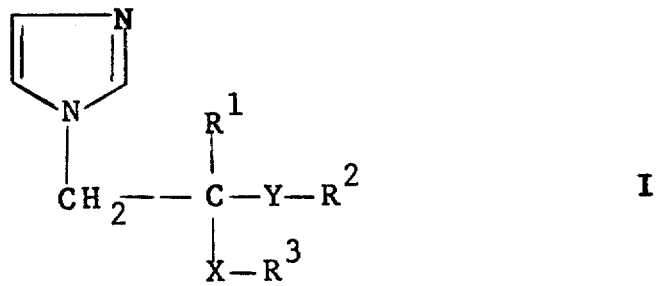   I

UNITED STATES PATENT AND TRADEMARK OFFICE
CERTIFICATE OF CORRECTION

PATENT NO. : 3,940,413
DATED : February 24, 1976
INVENTOR(S) : WOLFGANG KRAMER ET AL It is certified that error appears in the above-identified patent and that said Letters Patent are hereby corrected as shown below:

and pharmaceutically acceptable nontoxic salts thereof wherein $R^1$ and $R^3$ are the same or different, and are hydrogen, alkyl especially straight or branched-chain alkyl of 1 to 6 carbon atoms and especially 1 to 4 carbon atoms, alkenyl especially straight or branched chain alkenyl of 2 to 6 carbon atoms and especially 2 to 4 carbon atoms, cycloalkyl of 3 to 7 carbon atoms and especially of 3, 5 or 6 carbon atoms, cycloalkenyl of 5 to 7 carbon atoms especially 5 or 6 carbon atoms, aryl especially of 6 to 10 carbon atoms and particularly phenyl unsubstituted or substituted by 1 or more preferably 1 to 3 and especially 1 or 2 of the same or different sub-

UNITED STATES PATENT AND TRADEMARK OFFICE
CERTIFICATE OF CORRECTION

PATENT NO. : 3,940,413

DATED : February 24, 1976

INVENTOR(S) : WOLFGANG KRAMER ET AL

It is certified that error appears in the above-identified patent and that said Letters Patent are hereby corrected as shown below:

stituents selected from the group consisting of halogen especially fluorine, chlorine or bromine, halogenoalkyl of 1 or 2 carbon atoms in the alkyl moiety and 2 to 5 halogeno moieties especially chlorine or fluorine and particularly the trifluoromethyl moiety, straight or branched-chain alkyl of 1 to 4 carbon atoms, straight or branched-chain alkoxy of 1 to 4 carbon atoms, thioalkyl of 1 to 4 carbon atoms, alkylsulphonyl of 1 to 4 carbon atoms, nitro, cyano, phenyl and hydroxymethyl-substituted phenyl, or aralkyl particularly of 6 to 10 carbon atoms in the aryl moiety and 1 to 4 carbon atoms in the alkyl moiety especially benzyl, unsubstituted or substituted by 1 or more preferably 1 to

UNITED STATES PATENT AND TRADEMARK OFFICE
CERTIFICATE OF CORRECTION

PATENT NO. : 3,940,413  
DATED : February 24, 1976  
INVENTOR(S) : WOLFGANG KRAMER ET AL Page 4 of 4

It is certified that error appears in the above-identified patent and that said Letters Patent are hereby corrected as shown below:

3 and especially 1 or 2 substituents selected from the group consisting of halogen especially fluorine, chlorine or bromine, halogenoalkyl of 1 or 2 carbon atoms in the alkyl moiety and 2 to 5 halogeno moieties especially chlorine or fluorine and partic- Signed and Sealed this first Day of June 1976

[SEAL]

Attest:

RUTH C. MASON  
Attesting Officer

C. MARSHALL DANN  
Commissioner of Patents and Trademarks